(12) United States Patent
Ferreira et al.

(10) Patent No.: US 7,705,013 B2
(45) Date of Patent: Apr. 27, 2010

(54) USE OF CANTHIN-6-ONE, PLANT EXTRACTS CONTAINING SAME AND DERIVATIVES THEREOF IN THE TREATMENT OF TRYPANOSOMIASES

(75) Inventors: Maria Elena Ferreira, Luque (PY); Alain Fournet, Ossages (FR); Antonieta Rojas De Arias, Atilio Pena (PY); Reynald Hocquemiller, Limours (FR); Erwan Poupon, Antony (FR)

(73) Assignees: Institut de Recherche pour le Developpement, Paris Cedex (FR); Universite Nationale d'Asuncion, Asuncion (PY)

( * ) Notice: Subject to any disclaimer, the term of this patent is extended or adjusted under 35 U.S.C. 154(b) by 1101 days.

(21) Appl. No.: 10/535,430

(22) PCT Filed: Nov. 24, 2003

(86) PCT No.: PCT/FR03/03459

§ 371 (c)(1),
(2), (4) Date: Feb. 22, 2006

(87) PCT Pub. No.: WO2004/050092

PCT Pub. Date: Jun. 17, 2004

(65) Prior Publication Data

US 2007/0149461 A1    Jun. 28, 2007

(30) Foreign Application Priority Data

Nov. 25, 2002 (FR) .................................. 02 14729

(51) Int. Cl.
*A61K 31/439* (2006.01)
*C07D 471/18* (2006.01)
(52) U.S. Cl. ........................................ 514/288; 546/66
(58) Field of Classification Search ................. 514/288; 546/66

See application file for complete search history.

(56) References Cited

FOREIGN PATENT DOCUMENTS

JP        02004790       *    1/1990

OTHER PUBLICATIONS

Ma, Z. et al.: Alkaloids and phenylpropanoids from Peganum nigellastrum. Phytochemistry, vol. 53, pp. 1075-1078, 2000.*
Mitscher, L. et al.: Antimicrobial agents from higher plants. Heterocycles, vol. 3, pp. 7-14, 1975.*
Nelson, E. et al.: Alkaloids of the Australian Rutaceae. Aust. J. of Scientific Research, A5, pp. 768-781, 1952.*
"Antimicrobial Alkaloids from a Nigerian Chewing Stick (*Fagara zanthoxyloides*)," O.O. Odebiyi and E. A. Sofowora, 1979, vol. 36, pp. 204-207.
"Constitutents of *Zanthoxylum rugosum* St.-Hil & Tul," Eliana Elisabeth Diehl et al., Biochemical Systematics and Ecology 28 (2000) 275-277.
"Canthin-6-one and β-carboline alkaloids from *Eurycoma harmandiana*," Tripetch Kanchanapoom et al., Phytochemistry 56 (2001) 383-386.
"Canthin-6-one Alkaloids from *Brucea antidysenterica* Root Bark," A. Harris et al., 1984, Pharmacological Studies of Piperine.
"Plants as Sources of Antimalarial Drugs. Part 3[1] *Eurycoma longifolia*," Kit L. Chan et al., 1985, Plants as Sources of Antimalarial Drugs.
"Synthesis And Antitumor Activity of Canthin-5,6-Dione Derivatives," Kazuo Koike et al., Heterocycles, vol. 51, No. 2, 1999.
"Evaluation of African medicinal plants for their in vitro trypanocidal activity," F. Freiburghaus et al., Journal of Ethnopharmacology 55 (1996) 1-11.
"In vitro trypanocidal activity of some rare Tanzanian medicinal plants," F. Freiburghaus et al., Acta Tropica 67 (1997) 181-185.

* cited by examiner

*Primary Examiner*—Charanjit S Aulakh
(74) *Attorney, Agent, or Firm*—William E. Beaumont

(57) ABSTRACT

A method of treating trypanosomiasis in a mammal, which entails administering to a mammal in need thereof an effective amount of medicinal producting comprising a plant extract comprising one or more compounds of formula (I).

29 Claims, 3 Drawing Sheets

**Effect of treatment with canthin-6-one or benznidazole on Pearl Bright mice infected with *T. cruzi*. Serological evaluation (ELISA assay)**

USE OF CANTHIN-6-ONE, PLANT EXTRACTS CONTAINING SAME AND DERIVATIVES THEREOF IN THE TREATMENT OF TRYPANOSOMIASES

FIELD OF THE INVENTION

The invention relates to the use of canthin-6-one, plant extracts containing same and some derivatives thereof for producing a medicinal product intended for the treatment of trypanosomiases, in particular for the treatment of Chagas' disease.

DESCRIPTION OF THE BACKGROUND

In Latin America, approximately 90 million individuals live in regions where Chagas' disease is endemic. Approximately 18 to 20 million individuals are already infected with the agent responsible for this disease: *Trypanozoma (Schizotrypanum) cruzi*.

Chemotherapeutic treatments for this disease are at the current time based on two families of molecules: nitrofurans, for instance nifurtimox, and nitroimidazoles, for instance benznidazole. These compounds can be effective on Chagas' disease at the beginning of infection, but they are barely effective, or not at all, on this disease when *Trypanosoma cruzi* has become established in the organism and the disease has taken on a chronic nature.

At this stage, this disease is at the current time considered to be incurable.

Treatments with nufurtimox and with benznidazole are also confronted with the appearance of resistant strains of *Trypanosoma cruzi*, which further decreases their effectiveness in the primary phase of Chagas' disease. Finally, these two molecules have not insignificant side effects such as anorexia, vomiting, peripheral neuropathy and allergic dermopathy.

There was therefore a need for a treatment for Chagas' disease that is effective both in the first phase of the disease, where *Trypanosoma cruzi* is present essentially in the blood, and in the second phase of this disease, where *Trypanosoma cruzi* is essentially found in the organs: heart, digestive system.

Canthin-6-one is a known compound that was isolated from plants such as: *Ailanthus altissima* (Simaroubaceae) by Ohmoto et al., Chem. Pharm. Bull., 1976, 24, 1532-1536; *Brucea antidysenterica* (Simaroubaceae) by Fukamiya et al., Planta Med., 1987, 53, 140-143; *Eurycoma harmandiana* (Simaroubaceae) by Kachanapoom et al., Phytochemistry, 2001, 56, 383-386; *Peganum nigellastrum* (Zygophyllaceae) by Ma et al., Phytochemistry, 2000, 53, 1075-1078.

Canthin-6-one has been identified in an extract of *Zanthoxylum elephantiasis* (Rutaceae) by Mitscher et al., Lloydia, 1972, 35, 177-180.

Therapeutic activities of canthin-6-one or of plant extracts containing it have been reported in the following indications:

The treatment of malaria, by Kordona et al., J. Nat. Prod., 1991, 54(5), 1360-1367; as an antitumor agent, by Fukamiya et al., Planta Med., 1987, 53(2), 140-143; as an antifungal agent by Mitscher et al., Lloydia, 1972, 35(2), 177-180.

*Zanthoxylum chiloperone*, from where the canthin-6-one for the use of the invention is extracted, is known for its use in traditional medicine as an anti-inflammatory, as an antipyretic, against rheumatism, and as a general antiparasitic.

However, nothing in the prior art implied that canthin-6-one was capable of constituting a treatment for Chagas' disease, both in its primary or acute phase and in its chronic phase.

A subject of the invention is therefore the use of canthin-6-one, of plant extracts containing it and of some of its derivatives, which will be defined below, for producing a medicinal product intended for the treatment of trypanosomiases, in particular the treatment of Chagas' disease.

Canthin-6-one was isolated from the bark of the trunk of a rutacea identified as *Zanthoxylum chiloperone* var. *angustifolium*.

This plant was harvested in Paraguay, close to Piribebuy in the department of Cordillera. An example of this plant was registered with the Herbarium of the Faculty of Chemistry of Asuncion in Paraguay under the number AF917.

Several extracts of *Zanthoxylum chiloperone* var. *angustifolium* were isolated by means of a method that will be described below. Canthin-6-one itself was also isolated from this plant. However, the invention can also be implemented using canthin-6-one isolated from the other plants that contain it, and that were listed above. Extracts of *Ailanthus altissima*, of *Brucea antidysenterica*, of *Eurycoma harmandiana*, of *Peganum nigellastrum* or of *Zanthoxylum elephantiasis* that contain it can also be used to implement the invention.

DETAILED DESCRIPTION OF THE PREFERRED EMBODIMENTS

Figure 1:
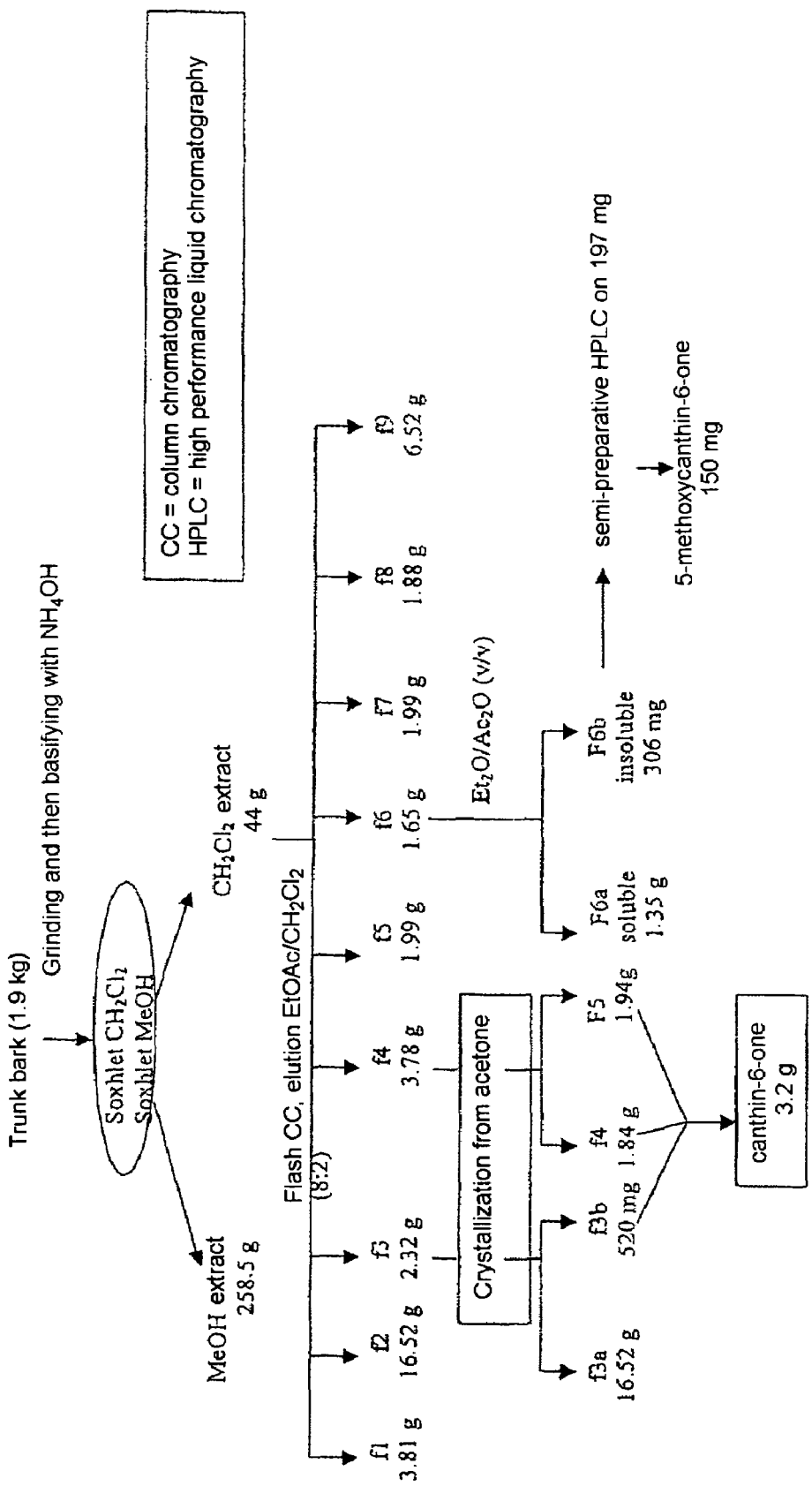
FIG. 1 illustrates a scheme for extraction of *Zanthoxylum chiloperone* (Rutaceae) bark.

According to a preferred embodiment of the invention, the extraction of *Zanthoxylum chiloperone* var. *angustifolium* and the isolation of the canthin-6-one were carried out according to a method comprising a first step that consists in grinding the dried bark of the trunk of *Zanthoxylum chiloperone* var. *angustifolium* and then in treating it with an aqueous alkaline solution, for instance with an aqueous ammonia solution.

The mixture obtained is extracted with a chlorinated organic solvent, for instance dichloromethane.

The canthin-6-one can then be isolated and purified by means well known to those skilled in the art, such as extraction, washing, chromatography, precipitation or recrystallization.

The same method or a similar method can be used on other plants containing canthin-6-one, in order to obtain extracts thereof comprising canthin-6-one or to isolate this compound.

Other compounds derived from canthin-6-one can be isolated from the plants mentioned above by similar methods. Canthin-6-one derivatives can also be prepared by methods of synthesis well known to those skilled in the art, using canthin-6-one or any other suitable compound as starting product. In particular, the invention relates to the derivatives corresponding to formula (I) below, and to their use for producing a medicinal product intended for the treatment of trypanosomiasis:

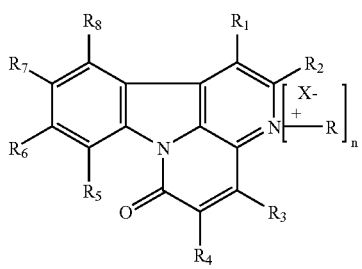

(I)

In formula (I), $R_1$, $R_2$, $R_3$, $R_4$, $R_5$, $R_6$, $R_7$ and $R_8$ represent, independently of one another:
- a hydrogen atom
- a saturated or unsaturated, linear, branched or cyclic $C_1$-$C_{12}$ alkyl group,
- a halogen atom chosen from chlorine, fluorine, bromine and iodine,
- a halo($C_1$-$C_{12}$)alkyl group in which the alkyl chain may be linear, branched or cyclic, and saturated or unsaturated, and the halogen atom(s) is (are) chosen from fluorine, chlorine, bromine and iodine,
- a hydroxyl function,
- a nitro function —NO,
- a cyano function —CN,
- a function —SH,
- a carboxylic acid function —COOH,
- an amide function —CONH$_2$,
- an amine function —NH$_2$,
- a $C_1$-$C_{12}$ alkoxy function in which the alkyl group may be linear, branched or cyclic, and saturated or unsaturated,
- a $C_1$-$C_{12}$ alkyl ester function, in which the alkyl group may be linear, branched or cyclic, and saturated or unsaturated,
- a secondary or tertiary alkylamide function, in which the $C_1$-$C_{12}$ alkyl group(s) may be linear, branched or cyclic, and saturated or unsaturated,
- a secondary or tertiary alkylamine function, in which the $C_1$-$C_{12}$ alkyl group(s) may be linear, branched or cyclic, and saturated or unsaturated,
- a $C_1$-$C_{12}$ alkylthio function, in which the alkyl group may be linear, branched or cyclic, and saturated or unsaturated,
- a $C_2$-$C_6$ heterocyclic group containing 1 to 4 hetero atoms chosen from sulfur, nitrogen and oxygen,
- a group —SO$_2$—NR'R" or a group —NR'—SO$_2$—R", in which R' and R" represent, independently of one another, a saturated or unsaturated, linear, branched or cyclic $C_1$-$C_{12}$ alkyl group;
- n represents 0 or 1;
- R represents a saturated or unsaturated, linear, branched or cyclic $C_1$-$C_{12}$ alkyl group;
- X$^-$ represents an anion that can be chosen from inorganic or organic anions such as, for example, the Cl$^-$ ion, the Br$^-$ ion, the I$^-$ ion, the S$^-$ ion, the PO$_3^-$ ion, the NO$_3^-$ ion, the acetate ion, the oxalate ion, the tartrate ion, the succinate ion, the maleate ion, the fumarate ion, the gluconate ion, the citrate ion, the malate ion, the ascorbate ion and the benzoate ion.

Canthin-6-one corresponds to formula (I) in which:
$R_1=R_2=R_3=R_4=R_5=R_6=R_7=R_8=H$ and n=0.

A subject of the invention is therefore a compound corresponding to formula (I) as defined above, in which at least one of $R_1$, $R_2$, $R_3$, $R_4$, $R_5$, $R_6$, $R_7$ and $R_8$ is different from H or else in which n=1.

A subject of the invention is also a medicinal product comprising a compound corresponding to formula (I) as defined above, in which at least one of $R_1$, $R_2$, $R_3$, $R_4$, $R_5$, $R_6$, $R_7$ and $R_8$ is different from H, or else in which n=1, in a pharmaceutically acceptable support.

Preferably, a subject of the invention is one of the compounds of formula (I) in which one or more of the conditions below are satisfied:
- $R_3$ represents an NH$_2$ group or a $C_1$-$C_{12}$ alkylamine group or a $C_1$-$C_{12}$ alkylamide group or a $C_2$-$C_6$ heterocycle comprising at least one amine function;
- $R_4$ represents a hydroxyl group or a $C_1$-$C_{12}$ alkoxy group;
- $R_1=R_2=R_5=R_6=R_7=R_8=H$.

Even more preferably, a subject of the invention is one of the compounds of formula (I) in which one or more of the conditions below are satisfied:
- $R_3$ represents an NH$_2$ group or a $C_1$-$C_6$ alkylamine group or a $C_1$-$C_6$ alkylamide group or a $C_2$-$C_6$ heterocycle comprising at least one amine function;
- $R_4$ represents a hydroxyl group or a $C_1$-$C_6$ alkoxy group;
- $R_1=R_2=R_5=R_6=R_7=R_8=H$.

Even more preferably, a subject of the invention is one of the compounds of formula (I) in which one or more of the conditions below are satisfied:
- $R_3$ represents an NH$_2$ group;
- $R_4$ represents an OCH$_3$ group;
- $R_1=R_2=R_5=R_6=R_7=R_8=H$.

According to another preferred variant of the invention, the compound of the invention is chosen from the compounds of formula (I) in which $R_1=R_2=R_3=R_4=R_5=R_6=R_7=R_8=H$ and n=1. According to this variant, R is advantageously a $C_1$-$C_6$ alkyl group. Even more advantageously, R is chosen from methyl and ethyl groups.

Advantageously, the compound of formula (I) is chosen from:
- 4-aminocanthin-6-one;
- N-methylcanthin-6-one iodide;
- 5-methoxycanthin-6-one.

The molecules of the invention can be obtained by following one of the synthetic pathways summarized in the schemes below. The preparation examples given in the experimental section also illustrate pathways for obtaining these compounds. The adaptation of these synthetic pathways to the various products corresponding to formula (I) calls upon the general knowledge of those skilled in the art.

Scheme 1:

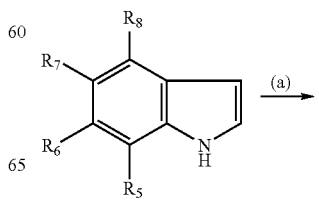

(a)

-continued

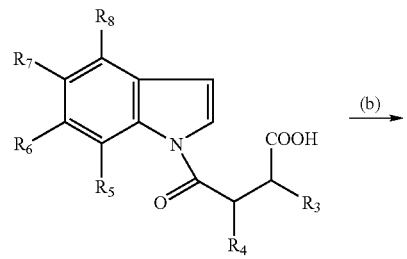

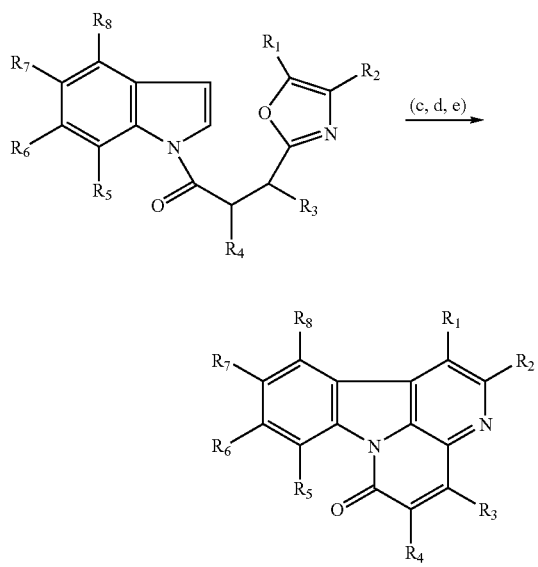

Legend: (a) substituted succinic anhyride;
(b) formation of substituted oxazoles;
(c) aza-Diels-Alder reaction;
(d) dehydration;
(e) oxidation of the 4–5 linkage.

Scheme 2:

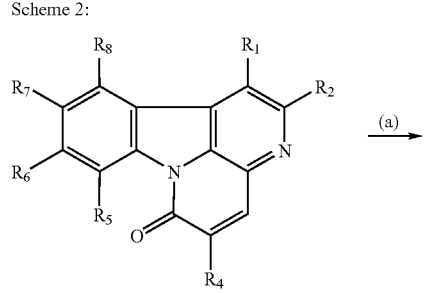

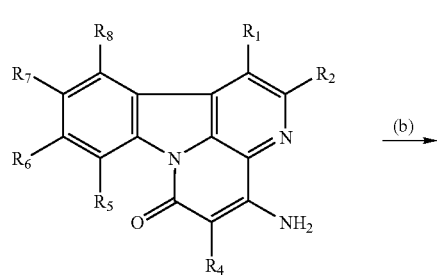

-continued

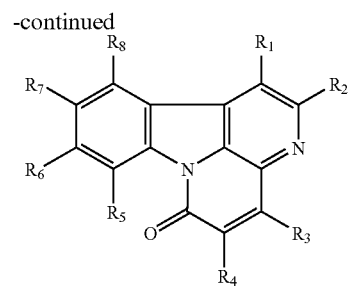

Legend: (a) see example 2 below;
(b) modifications of the primary amine function.

Scheme 3:

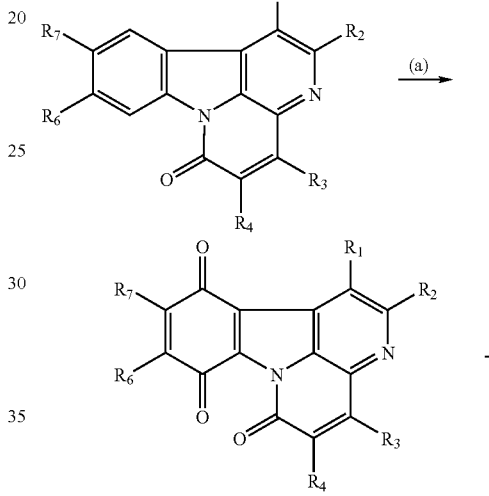

Legend: (a) oxidation to quinone;
(b) reduction;
(c) derivatizations or modifications of the hydroxyls.

Two forms of trypanosomiases are known, one is caused by the agent *Trypanosoma brucei* and is more well known under the name sleeping sickness, the other is caused by the agent *Trypanosoma cruzi* and is known as Chagas' disease. The invention is preferentially interested in the preparation of an effective treatment against *Trypanosoma cruzi*.

In the activity assays that are disclosed in detail below, canthin-6-one showed surprising effectiveness against *Trypanosoma cruzi*, in particular at doses ten times lower than the doses at which benznidazole is effective.

According to the invention, canthin-6-one, plant extracts containing it, or canthin-6-one derivatives, such as those corresponding to formula (I) defined above, will be used for treating infected individuals with trypanosomiasis, in particular for treating individuals infected with *Trypanosoma cruzi*, at a dose of between 0.01 and 100 mg/kg/d of canthin-6-one or of a derivative of formula (I), preferably of between 0.1 and 50 mg/kg/d, even more preferably of between 1 and 20 mg/kg/d.

Advantageously, the treatment will be formulated in the form of daily doses comprising from 0.2 mg to 1 g of canthin-6-one or of a derivative of formula (I), preferably from 2 to 500 mg, even more preferably from 5 to 200 mg.

The canthin-6-one, the plant extracts containing it and its derivatives of formula (I) can be administered orally or parenterally, combined with any appropriate pharmaceutical carrier. Preferably, the canthin-6-one, the plant extracts containing it and its derivatives of formula (I) are administered orally.

The invention will be understood more clearly from the following examples intended to illustrate it.

EXAMPLES

Materials and methods

The UV spectra were obtained on a Philips PU 8720 spectrometer. The IR spectra were measured on a Perkin-Elmer 257 spectrometer in KBr pellets. The $^1$H and $^{13}$C NMR spectra (CDCl$_3$) were obtained on a Bruker AC-200 or AC-400 device at a frequency of 200 and 50 MHz, respectively, or of 400 and 100 MHz, respectively. The EIMS and CIMS (methane) were measured on a Nermag R10-10C spectrometer. The semi-preparative HPLC was carried out using Waters 590 detector connected to an ABB SE 120 recording device, with a Millipore-Waters system (Milford Mass., USA) equipped with a 590 pump, an SSV injector and a Millipore C$_{18}$ Prepak 1000 column.

Example 1

Isolation of canthin-6-one and of 5-methoxycanthin-6-one

The *Zanthoxylum chiloperone* bark extraction method is represented in FIG. 1:

The dried bark of the trunk of *Zanthoxylum chiloperone* (1.9 kg) is treated with dichloromethane in a Soxhlet device, so as to give, after evaporation of the solvent, 44 g of plant extract. This extract is redissolved and then purified by flash chromatography on a silica column using an ethyl acetate/dichloromethane (8:2) mixture as eluent. 9 fractions, each of 250 ml, numbered 1 to 9 in the order of elution, are recovered. Fractions f$_{3b}$ to f$_5$ are combined to give 3.2 g of canthin-6-one after evaporation of the solvents and crystallization from acetone.

Fraction f$_6$ is purified by preparative HPLC using as solvent a mixture of methanol and water (7:3), to give 150 mg of 5-methoxycanthin-6-one after crystallization from acetone.

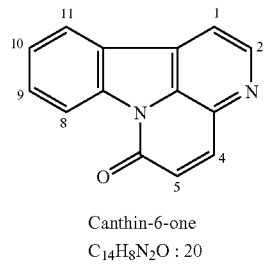

Canthin-6-one
C$_{14}$H$_8$N$_2$O : 20

The canthin-6-one crystallizes from acetone in the form of pale yellow needles.

The melting point (Mp), determined on a Köfler bench, is 162° C.

UV spectrum: MeOH$_{max}$ (log ε) (in MeOH at 0.05 g/l): 225 (1.70), 251 (1.35), 260 (1.40), 268 (1.40), 362 (1.33), 379 (1.29); (+0.5N HCl): 225 (non-determinable), 266 (1.49), 273 (1.49), 304 (1.56), 360; (+1N NaOH): 225 (non-determinable) 251 (1.54), 259 (1.55), 267 (1.50), 362 (1.33), 379 (1.29).

IR spectrum: 1665, 1630 cm$^{-1}$ $^1$H NMR spectrum: 400 MHz (CDCl$_3$)_ppm: 6.90 (d, 1H, J=9.8 Hz, H$_5$); 7.50 (td, 1H, J=8.5; 7.5 and 1 Hz, H$_{10}$); 7.70 (td, 1H, J=8.2; 8.5 and 1 Hz, Hg); 7.90 (d, 1H, J=5 Hz, H$_1$); 8.00 (d, 1H, J=9.8 Hz, H$_4$); 8.10 (dt, 1H, J=7.5 and 1 Hz, H$_{11}$); 8.65 (dt, 1H, J=8.2 and 1 Hz, H$_8$); 8.80 (d, 1H, J=5 Hz, H$_2$).

$^{13}$C NMR spectrum: 50 MHz (CDCl$_3$)_ppm: 116.4 (C$_1$H), 117.2 (C$_8$H), 122.6 (C$_{11}$H), 124.3 (C$_{12}$), 125.7 (C$_{10}$H) 129.0 (C$_5$H), 130.1 (C$_{13}$), 130.7 (C$_9$H), 131.9 (C$_{14}$), 136.2 (C$_{3a}$) 139.3 (C$_{7a}$), 139.6 (C$_4$H), 145.9 (C$_2$H), 159.0 (C$_6$).

Mass spectrum: [ion fragment] m/z (%) [M+Na]$^+$ 243 (100%).

Elemental Analysis: C, 76.42; H, 3.68; N, 12.86%.

Example 2

Process of synthesizing canthin-6-one derivatives 4-aminocanthin-6-one:

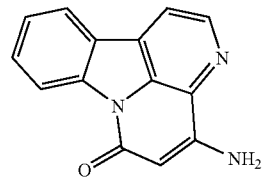

C$_{14}$H$_9$N$_3$O - MW 235

The canthin-6-one (100 mg-0.45 mmol) is suspended in a saturated solution of sodium azide (50 ml). Dimethylformamide is added until a clear solution is obtained. An excess of zinc bromide is added (1 g) and the medium is brought to reflux until the starting product has been consumed (reaction followed by thin layer chromatography, 9:1 CH$_2$Cl$_2$/MeOH). The cooled reaction medium is greatly diluted with water and then extracted with dichloromethane (4 times). The combined organic phases are dried (Na$_2$SO$_4$) and then concentrated under reduced pressure. The 4-aminocanthin-6-one is purified by flash chromatography on a silica column (0.3 bar, elution: 95:5 CH$_2$Cl$_2$/MeOH), 74 mg (70%).

A powdery yellow solid is obtained: $^1$H NMR spectrum (400 MHz, CDCl$_3$): δ ppm, 4.9 (s, 2H); 7.0 (s, 1H); 7.5 (t, J=7.6 Hz, 1H); 7.7 (m, 2H); 8.05 (d, J=7.6 Hz 1H); 8.65 (d, J=8.1 Hz, 1H); 8.7 (d, J=5.1 Hz, 1H); $^{13}$C NMR spectrum (100 MHz, CDCl$_3$): δ ppm, 106.8; 112.0; 117.0; 122.6; 125.7; 125.8; 126.5; 129.1; 130.1; 138.8; 139.1; 142.4; 145.9; 156.2; infrared spectrum (v, cm$^{-1}$): 3254, 1673, 1612, 1580, 1556, 1443, 1333, 1313; mass spectrum (electrospray, m/z): 236 [M+H$^+$]; Mp (CH$_2$Cl$_2$): 199-200° C.; R$_f$=0.6 (9:1 CH$_2$Cl$_2$/MeOH).

N-methylcanthin-6-one iodide

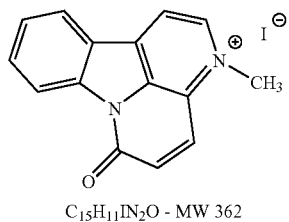

C$_{15}$H$_{11}$IN$_2$O - MW 362

The canthin-6-one (100 mg-0.45 mmol) is dissolved in methyl iodide (1 ml). The solution is stirred at ambient temperature until the starting product has been consumed (reaction followed by thin layer chromatography, 9:1 CH$_2$Cl$_2$/MeOH). The precipitate is collected by filtration and washed with dichloromethane (150 mg-90%).

An orange powder is obtained, $^1$H NMR spectrum (400 MHz, DMSO-d$_6$): δ ppm, 4.6 (s, 3H); 7.4 (d, J=10.0 Hz, 1H); 7.7 (t, J=7.7 Hz, 1H); 8.0 (t, J=7.8 Hz, 1H); 8.6 (m, 3H); 8.9 (d, J=6.3 Hz, 1H); 9.1 (d, J=6.3 Hz, 1H); $^{13}$C NMR spectrum (100 MHz, CDCl$_3$): δ ppm, 44.3; 116.8; 119.1; 122.5; 125.7; 127.4; 127.5; 130.2; 133.3; 133.7; 134.7; 136.1 141.4; 142.7; 158.0; infrared spectrum (v, cm$^{-1}$): 1684, 1655, 1340, 1257, 1142; mass spectrum (electrospray, m/z): 235 [M$^+$]; Mp (CH$_2$Cl$_2$): 240° C.

Example 3

Methodology of the In Vivo Trials on *Trypanosoma cruzi* in the Acute Phase

Animals and parasites: The Balb/c-type mice are bred in the animal house of the Health Sciences Research Institute (IICS, Asuncion, Paraguay) and are 6 to 8 weeks old at the time of the experimental protocols.

For these trials, the CL strain (Brener clone) of *T. cruzi* is used in the circulating form of the parasite (trypomastigotes). The animals are infected intraperitoneally with 5000 parasites; this strain produces its parasite peak 21 to 25 days after infection. Each week, the number of parasites is verified by means of a blood sample taken from the tail of the mouse.

Infection and treatment: The treatments with benznidazole, the reference medicinal product, and canthin-6-one begin 11 days after parasitic infection, at a rate of 50 mg/kg or 200 mM/kg for benznidazole and at the concentration of 5 mg/kg or 20 mM/kg for canthin-6-one. The duration of the treatments is fixed at two weeks and the chosen route of administration is oral for benznidazole and canthin-6-one; furthermore, a group of mice is treated with canthin-6-one administered subcutaneously. The untreated and infected mice are given 100 μl of a phosphate buffered saline solution.

Criteria for Evaluating Treatment Effectiveness:
- weekly counting of the number of parasites circulating in the peripheral blood throughout the experiment, i.e. 10 weeks;
- observation of mortality;
- two serological evaluations: 40 days post-infection, i.e. 15 days after treatment has been stopped, and 68 days post-infection, i.e. 45 days post-treatment. The serological evaluation is carried out by means of a Chagas ELISA assay (enzyme linked immunoassay) kit, IISC, Asuncion. The optical densities are measured with an ELISA plate reader (Titerek, Unistan, I).

Statistical studies: The mean and the standard deviations of each group are calculated, the differences between the groups are determined by means of the Student's test and the Kruskal-Wallis non-parametric analysis of variance test. The comparisons are carried out between the nontreated group and the treated groups, P<0.05.

Figure 2:
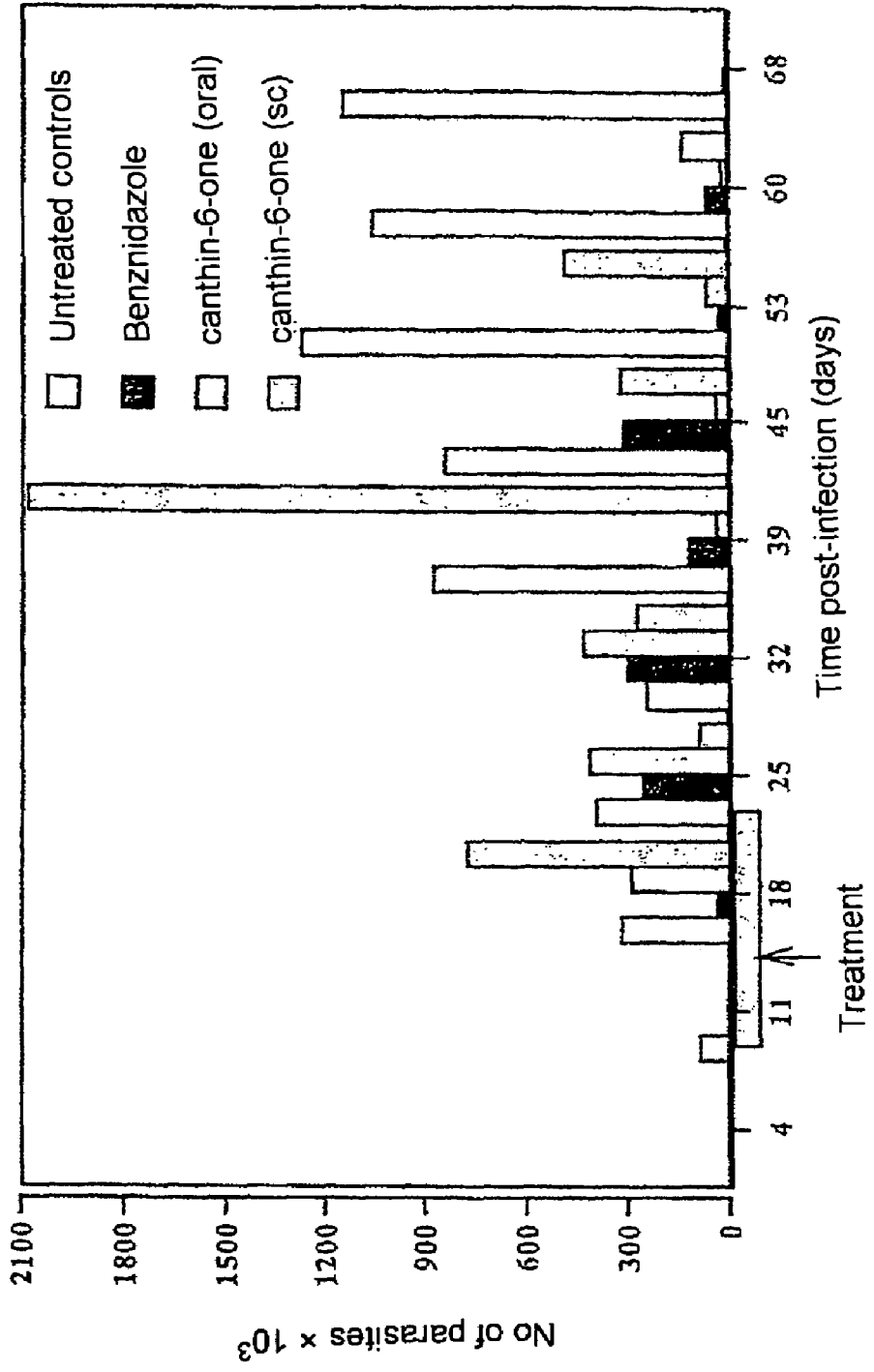
FIG. 2 shows the effectiveness of canthin-6-one and of benznidazole on mice experimentally infected with *Trypanosoma cruzi*.
Figure 3:
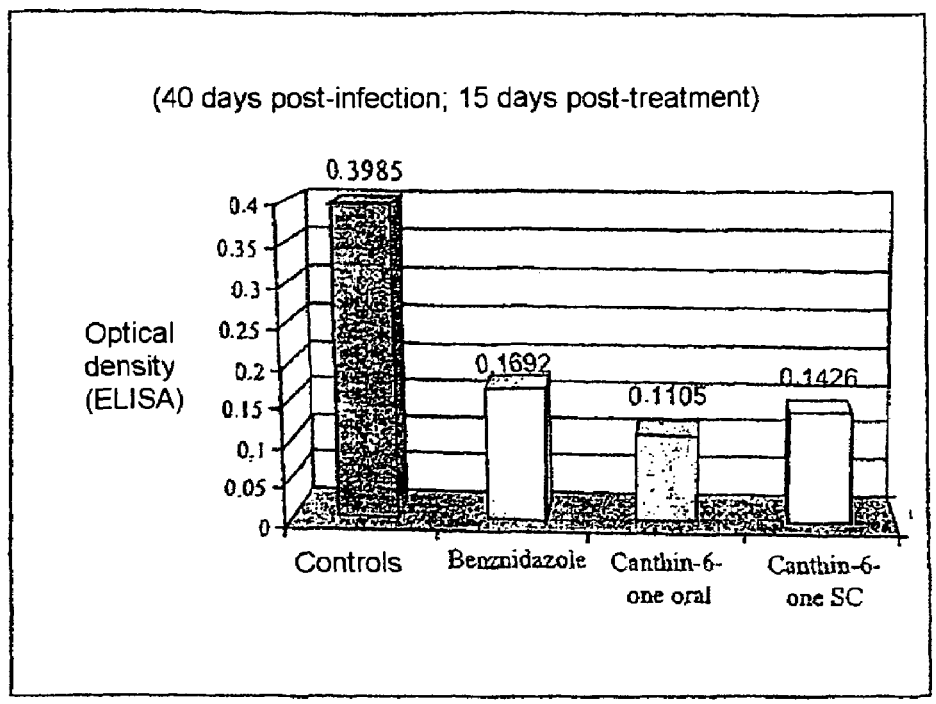
FIG. 3 shows the effect of treatment with canthin-6-one or benznidazole on Pearl Bright mice infected with *T. cruzi*. Serological evaluation (ELISA assay) at 40 days post infection and 15 days post treatment.
Figure 4:
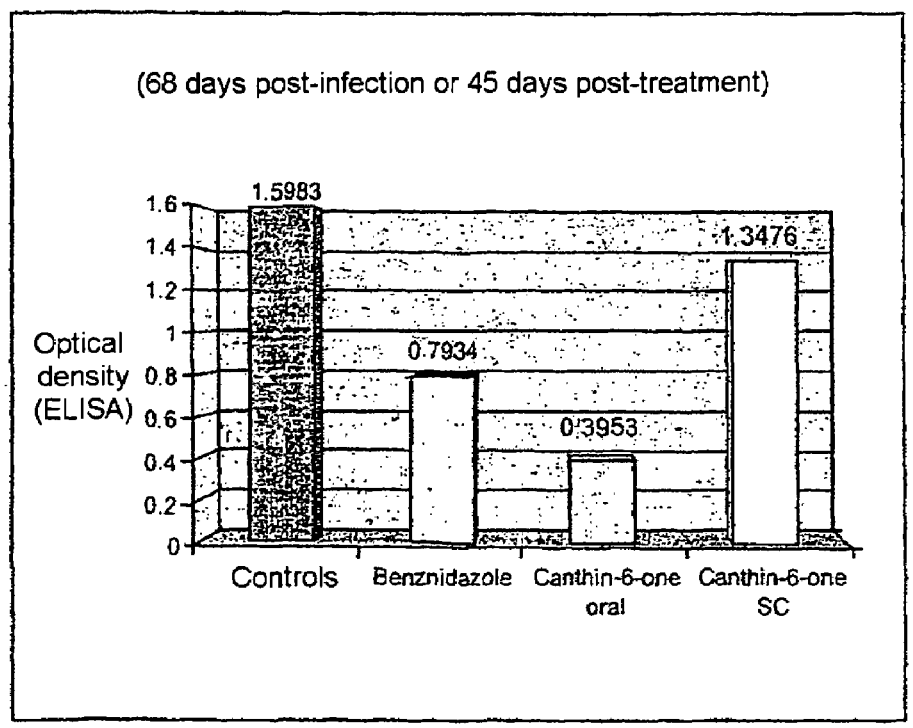
FIG. 4 shows the effect of treatment with canthin-6-one or benznidazole on Pearl Bright mice infected with *T. cruzi*. Serological evaluation (ELISA assay) at 68 days post-infection or 45 days post-treatment.

The results are given in Tables I and II and in FIGS. 2, 3 and 4.

TABLE I

Effectiveness of canthin-6-one and of benznidazole on mice infected experimentally with *Trypanosoma cruzi* Parasitological evaluation (number of parasites ± standard deviation)

| Days post-infection | Untreated controls (n = 8) | Benznidazole (n = 8) | Oral canthin-6-one (n = 7) | Subcutaneous canthin-6-one (n = 8) |
|---|---|---|---|---|
| 4 | 0 | 0 | 0 | 0 |
| 11* | 90.9 ± 257 | 0 | 0 | 0 |
| 18* | 313.6 ± 468.7 | 34.9 ± 98.6 | 285 ± 515.9 | 766.3 ± 719.2 |
| 25* | 387.3 ± 671.1 | 250.1 ± 503.5 | 402 ± 837.7 | 88.4 ± 142.9 |
| 32 | 242.1 ± 553.2 | 296.8 ± 625.5 | 426.2 ± 664.5 | 267.5 ± 546.5 |
| 39 | 870.5 ± 1902.1 | 118.3 ± 192.9 | 36.6 ± 58.4 | 2077.1 ± 2214.2 |
| 45 | 835.8 ± 1002.7 | 300.8 ± 431.6 | 34.4 ± 76.9 P = 0.05 | 314.1 ± 499.3 |
| 53 | 1273.3 ± 1647.8 | 23.3 ± 65.8 P = 0.01 | 58.4 ± 80.6 P = 0.05 | 473.4 ± 921.9 |
| 60 | 1050.1 ± 2605.5 | 65.3 ± 93.2 | 16 ± 35.8 P < 0.05 | 129.9 ± 194.4 |
| 68 | 1144.1 ± 1641.9 | 9.4 ± 26.5 P = 0.03 | 0 P = 0.02 | 34.9 ± 98.6 P = 0.03 |

*Period of treatment (two weeks)
n = number of mice

TABLE II

Effect of the treatment with canthin-6-one or of benznidazole on Balb/c mice infected with *T. cruzi* Serological evaluation (ELISA assay)

| Treatment | No. of mice | Route of admin. | 1st serology ® | Negative serology/ survivor | 2nd serologyV | Negative serology/ survivor |
|---|---|---|---|---|---|---|
| Untreated controls (PBS) | 8 | Oral | 0.3985 ± 0.092 | 0/8 (0%) | 0.1598 ± 0.382.3 | 0/8 (0%) |
| Benznidazole (reference medicinal product) (50 mg) | 8 | Oral | 0.1692 ± 0.1179 $P < 0.001$ | 6/8 (75%) | 0.7934 ± 0.8607 $P < 0.05$ | 3/8 (37.5%) |
| Canthin-6-one (5 mg) | 7 | Oral | 0.1105 ± 0.0387 $P < 0.001$ | 7/7 (100%) | 0.3953 ± 0.7531 $P < 0.05$ | 3/7 (42.9%) |
| Canthin-6-one (5 mg) | 8 | SC | 0.2151 ± 0.1447 $P < 0.05$ | 4/7 (57.1%) | 0.1347 ± 0.6327 $P < 0.001$ | 2/6 (33.3%) |

Serology: anti-*T. cruzi* ELISA.
®40 days post-infection; 15 days post-treatment
V68 days post-infection; 45 days post-treatment
Value of P versus untreated controls.

As can be seen in FIG. 2, canthin-6-one administered orally at a dose of 5 mg/kg/d shows, from the 39th day after infestation and 15 days after the end of treatment, an activity that is much greater than the benznidazole used at the dose of 50 mg/kg/d. It allows complete eradication of *Trypanosoma cruzi* from the infected organism, something which benznidazole does not make it possible to obtain. These results are confirmed by the optical density measurement (ELISA) at 15 and 48 days after the end of treatment, as is illustrated in FIGS. 3 and 4.

Example 4

Methodology of the In Vivo Trials on *Trypanosoma cruzi* in the Chronic Phase

Animals and Parasites:

The Balb/c-type mice are bred in the animal house of the Health Sciences Research Institute (IICS, Asuncion, Paraguay) and are 6 to 8 weeks old at the time of the experimental protocols. For this experimental protocol, the CL strain (Brener clone) of *T. cruzi* is used in the circulating form (trypomastigotes), and the strain is maintained in routine culture on an animal model by passage every 14 days. The animals are infected intraperitoneally with 1000 parasites. Under these experimental conditions, the parasites develop slowly; this strain produces a parasite peak 21 to 28 days after infection. The majority of the mice survive (70-80%) with slight deterioration of their general physical condition and with absent or subpatent parasitemia. Each week, the number of parasites is verified by taking a blood sample from the tail of the mouse.

Infection and Treatments:

For this long-duration experiment, the treatments begin 120 days after parasitic infection, when the parasitemia is subpatent in all the mice. The mice are then divided up into groups randomly. The treatments with benznidazole, the reference medicinal product, are administered at a concentration of 50 mg/kg or 200 mM/kg per day for 20 days, orally. Canthin-6-one is administered either orally or subcutaneously at a concentration of 5 mg/kg or 20 mM/kg per day for 20 days. A total dichloromethane extract of Zanthoxylum chiloperone var. *angustifolium* trunk bark is administered orally or subcutaneously at a concentration of 50 mg/kg per day for 20 days. For administration, the active principles are dissolved in 50 μl of a phosphate buffered saline (PBS) solution. The untreated and infected mice receive 50 μl of PBS.

Criteria for Evaluating Treatment Effectiveness:
Weekly counting of the number of parasites circulating in the peripheral blood throughout the experiment, i.e. 30 weeks.
Observation of mortality.
Three serological evaluations, 45 days before the beginning of treatments, 10 days after treatment has stopped and 75 days post-treatment. The serological evaluation is carried out using a Chagas ELISA assay (enzyme linked immunoassay) kit, IISC, Asuncion. The optical densities are measured with an ELISA plate reader (Titerek, Unistan, I).

Statistical Studies:

The mean and the standard deviations of each group are calculated, and the differences between the groups are determined by means of the Student's test and the Kruskal-Wallis non-parametric analysis of variance test. The comparisons are carried out between the untreated group and the treated groups, $P<0.05$.

The results are given in Tables III and IV.

TABLE III

Parasitological therapies in mice infected chronically with *T. cruzi* and treated for 20 days with benznidazole (n = 5), canthin-6-one (n = 8) and a total extract of *Zanthoxylum chiloperone* var. *angustifolium* (n = 7)

| Treatment* | Negative parasitemia/number of surviving mice (number of days post-treatment) | | | |
|---|---|---|---|---|
|  | 0 | 10 d | 40 d | 60 d |
| Untreated control mice | 5/5 | 2/4 | 1/1 | 1/1 |
| Benznidazole (50 mg/kg/d) orally | 5/5 | 2/5 | 5/5 | 5/5 |
| Canthin-6-one (5 mg/kg) orally | 7/8 | 7/8 | 8/8 | 8/8 |
| Canthin-6-one (5 mg/kg/d) subcutaneously | 6/8 | 7/8 | 6/8 | 6/8 |
| Total extract of Z. chiloperone bark (50 mg/kg/d) orally | 7/7 | 7/7 | 7/7 | 7/7 |

TABLE III-continued

Parasitological therapies in mice infected chronically with
*T. cruzi* and treated for 20 days with benznidazole (n = 5),
canthin-6-one (n = 8) and a total extract of
*Zanthoxylum chiloperone* var. *angustifolium* (n = 7)

| Treatment* | Negative parasitemia/number of surviving mice (number of days post-treatment) | | | |
|---|---|---|---|---|
| | 0 | 10 d | 40 d | 60 d |
| Total extract of *Z. chiloperone* bark (50 mg/kg/d) subcutaneously | 4/6 | 4/6 | 5/5 | 3/5 |

*Treatments 108 days after parasitic infection

TABLE IV

Effect of treatment with canthin-6-one, a total extract
of *Zanthoxylum chiloperone* var. *angustifolium*, or benznidazole
on Balb/c mice chronically infected with *T. cruzi*.

| Treatment | ELISA (optical density ± standard deviation) Number of days post-treatment | | |
|---|---|---|---|
| | 43 days before treatment | 10 d | 75 d |
| Untreated control mice | 1.805 ± 0.075 | 1.913 ± 0.115 | 1.793* |
| Benznidazole (50 mg/kg/d) orally | 2.072 ± 0.220 | 1.712 ± 0.473 | 1.979 ± 0.350 |
| Canthin-6-one (5 mg/kg) orally | 1.878 ± 0.348 | 1.621 ± 0.547 | 1.799 ± 0.333 |
| Canthin-6-one (5 mg/kg/d) subcutaneously | 1.916 ± 0.368 | 1.850 ± 0.405 | 1.870 ± 0.268 |
| Total extract of *Z. chiloperone* bark (50 mg/kg/d) orally | 1.932 ± 0.228 | 1.890 ± 0.288 | 1.961 ± 0.172 |
| Total extract of *Z. chiloperone* bark (50 mg/kg/d) subcutaneously | 1.718 ± 0.264 | 1.703 ± 0.470 | 1.815 ± 0.374 |

*just one mouse alive at the end of the experiment

As can be seen in Table III, canthin-6-one administered orally, at a dose of 5 mg/kg/d for 20 days from the 108th day after parasitic infection, and 79 days after the end of the treatment, showed greater activity than benznidazole used at a dose of 50 mg/kg/d. It induces complete eradication of *Trypanosoma cruzi* from the infected organism and protects the mice against death. These results are confirmed by serology using the ELISA assay, at 10 and 75 days after the end of treatment, as is illustrated by the data in Table IV.

The invention claimed is:

1. A method of treating trypanosomiasis in a mammal, which comprises administering to a mammal in need thereof an effective amount of a medicinal product comprising a plant extract comprising one or more compounds of the formula (I):

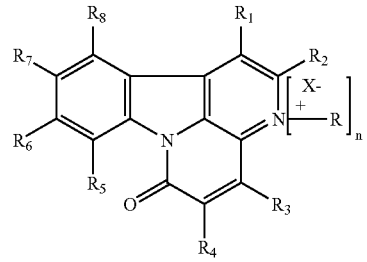

(I)

wherein R1, R2, R3, R4, R5, R6, R7 and R8 represent independently of one another:
a hydrogen atom;
a saturated or unsaturated, linear, branched or cyclic $C_1$-$C_{12}$ alkyl group;
a halogen atom;
halo($C_1$-$C_{12}$)alkyl, wherein an alkyl group thereof is linear, branched or cyclic, and saturated or unsaturated;
hydroxyl;
nitro;
cyano;
mercapto;
carboxylic acid;
amide;
amine;
$C_1$-$C_{12}$ alkoxy, wherein an alkyl group thereof is linear, branched or cyclic, and saturated or unsaturated;
$C_1$-$C_{12}$ alkyl ester, wherein an alkyl group thereof is linear, branched or cyclic, and saturated or unsaturated,
secondary or tertiary alkylamine, wherein an $C_1$-$C_{12}$ alkyl group(s) thereof is linear, branched or cyclic, and saturated or unsaturated;
secondary or tertiary alkylamide, wherein an $C_1$-$C_{12}$ alkyl group(s) thereof is linear, branched or cyclic, and saturated or unsaturated,
$C_1$-$C_{12}$ alkylthio, wherein an alkyl group thereof is linear, branched or cyclic, and saturated or unsaturated;
$C_2$-$C_6$ heterocyclic group containing 1 to 4 hetero atoms selected from the group consisting of sulfur, nitrogen and oxygen;
a group —$SO_2$—NR'R" or a group —NR'—$SO_2$—R", in which R' and R" represent, independently of one another, a saturated or unsaturated, linear, branched or cyclic C1-C12 alkyl group, with the proviso that one of $R_3$ or $R_4$ is other than hydrogen;
n represents 0;
R represents a saturated or unsaturated, linear, branched or cyclic $C_1$-$C_{12}$ alkyl group; and
X represents an anion, which is either an inorganic or organic anion.

2. The method of claim 1, wherein $R_3$ represents $NH_2$, $C_1$-$C_{12}$ alkylamine, $C_1$-$C_{12}$ alkylamide or $C_2$-$C_6$ heterocycle comprising at least one amine group.

3. The method of claim 1, wherein $R_4$ represents hydroxyl or $C_1$-$C_{12}$ alkoxy.

4. The method of claim 1, for treating trypanosomiasis in a chronic phase or an acute phase.

5. The method of claim 1, for treating Chagas' disease.

6. The method of claim 1, for treating trypanosomiasis caused by *Trypanosoma brucei*.

7. The method of claim 1, for treating trypanosomiasis caused by *Trypanosoma cruzi*.

8. The method of claim 1, wherein the medicinal product is administered at a dose of between about 0.01 and 100 mg/kg/d of compound of formula (I).

9. The method of claim 8, wherein the administered dose is between about 0.1 and 50 mg/kg/d.

10. The method of claim 9, wherein the administered dose is between about 1 and 20 mg/kg/d.

11. The method of claim 1, wherein the medicinal product is administered orally.

12. The method of claim 1, wherein the mammal is a human.

13. A method of treating trypanosomiasis in a mammal which comprises administering to a mammal in need thereof an effective amount of canthin-6-one.

14. The method of claim 13, wherein from 0.2 mg to 1 g of the canthin-6-one is administered per day.

15. The method of claim 13, wherein the mammal is a human.

16. A method of treating trypanosomiasis in a mammal, which comprises administering to a mammal in need thereof an effective amount of a medical product comprising a plant extract comprising canthin-6-one.

17. The method of claim 16, wherein the canthin-6-one is present in the form of an extract of a plant selected from the group consisting of *Ailanrhus altissima, Brucea antidysenterica, Eurycama harmandiana, Peganum nigellastrum, Zanthoxylum elephantiasis* and *Zanthoxylum chiloperone*.

18. The method of claim 17, wherein the canthin-6-one is present in the form of an extract of *Zanthoxylum chiloperone* var. *angustifolium*.

19. The method of claim 16, wherein the plant extract comprising canthin-6-one is obtained by a method comprising the first steps of grinding the dried bark of a trunk of *Zanthoxylum chiloperone* var. *angustifolium*, and then treating the ground dried bark with an aqueous alkaline solution.

20. The method of claim 19, wherein the plant extract comprising canthin-6-one is obtained by a method further comprising a second step comprising extracting the ground bark and aqueous alkaline solution with a chlorinated organic solvent.

21. The method of claim 16, for treating trypanosomiasis in a chronic phase or an acute phase.

22. The method of claim 16, for treating Chagas' disease.

23. The method of claim 16, for treating trypanosomiasis caused by *Trypanosoma brucei*.

24. The method of claim 16 for treating trypanosomiasis caused by *Trypanosoma cruzi*.

25. The method of claim 16, wherein the medicinal product is administered at a dose of between about 0.01 and 100 mg/kg/d of canthin-6-one.

26. The method of claim 25, wherein the administered dose is between about 0.1 and 50 mg/kg/d.

27. The method of claim 26, wherein the administered dose is between about 1 and 20 mg/kg/d.

28. The method of claim 16, wherein the medicinal product is administered orally.

29. The method of claim 16, wherein the mammal is a human.

* * * * *